(12) United States Patent
Athma et al.

(10) Patent No.: US 8,010,332 B2
(45) Date of Patent: Aug. 30, 2011

(54) HYDROPHOBIC MOMENT OF MULTI-DOMAIN PROTEINS

(75) Inventors: Prasanna Athma, Yorktown Heights, NY (US); Ajay Royyuru, Congers, NY (US); Benjamin David Silverman, Yorktown Heights, NY (US); Ruhong Zhou, Fort Lee, NJ (US)

(73) Assignee: International Business Machines Corporation, Armonk, NY (US)

( * ) Notice: Subject to any disclaimer, the term of this patent is extended or adjusted under 35 U.S.C. 154(b) by 1 day.

(21) Appl. No.: 12/540,540

(22) Filed: Aug. 13, 2009

(65) Prior Publication Data

US 2009/0306904 A1    Dec. 10, 2009

Related U.S. Application Data

(62) Division of application No. 10/921,493, filed on Aug. 19, 2004, now Pat. No. 7,877,214.

(51) Int. Cl.
*G06G 7/48* (2006.01)
*G01N 33/48* (2006.01)

(52) U.S. Cl. ............................................. 703/11; 702/19

(58) Field of Classification Search .......................... None
See application file for complete search history.

(56) References Cited

OTHER PUBLICATIONS

Eisenberg et al. "Hydrophobic moments and protein structure" Faraday Symp. Chem. Soc., (1982) vol. 17, pp. 107-120.*
Karplus "Hydrophobicity Regained" Protein Science (1997) vol. 6, pp. 1302-1307.*
R. Jaenicke, Stability and Folding of Domain Proteins, 71 Prog. Biophys. & Mol. Biol. 155-241 (1999).
C. Anselmi, et al., Identification of Protein Domains on Topological Basis, 58 Biopolymers 218-229 (2001).
S.J. Wheelan et al., Domain Size Distributions Can Predict Domain Boundaries, 16 Bioinformatics 613-618 (2000).
A.G. Murzin et al., SCOP: A Structural Classification of Protein Database for the Investigation of Sequences and Structures, 247 J. Mol. Biol. 536-540 (1995).
B.D. Silverman, Hydrophobic Moments of Protein Structures: Spatially Profiling the Distribution, 98 Proc. Natl. Acad. Sci. USA 4996-5001 (2001).
R. Zhou et al., Spatial Profiling of Protein Hydrophobicity: Native vs. Decoy Structures, 52 Proteins: Struc. Funct. & Genetics 561-572 (2003).
D. Eisenberg et al., The Helical Hydrophobic Moment: A Measure of the Amphiphilicity of a Helix, 299 Nature 371-374 (1982).
D. Eisenberg et al., Analysis of Membrane Protein Sequences with the Hydrophobic Moment Plot, 179 J. Mol. Biol. 125-142 (1984).
H.J. Pownall et al., Helical Amphipathic Moment: Application to Plasma Lipoproteins, 159 FEBS 17-23 (1983).
I. Tsigelny at al., Mechanism of Action of Chromogranin A On Catecholamine Release: Molecular Modeling of the Catestatin Region Reveals a -strand/loop/ -strand Structure Secured by Hydrophobic Interactions and Predictive of Activity, 77 Regulatory Peptides 43-53 (1998).
J.P. Pardo et al., An Alternative Model for the Transmembrane Segments of the Yeast H+-ATPase, 15 Yeast 1585-1593 (1999).
P.W. Mobley et al., Membrane Interactions of the Synthetic N-Terminal Peptide of HIV-1 gp41 and Its Structural Analogs, 1418 Biochimica et Biophysica Acta 1-18 (1999).
L. Thong et al., Flexible Programs for the Prediction of Average Amphiphilicity of Multiply Aligned Homologous Proteins: Application to Integral Membrane Transport Proteins, 16 Molecular Membrane Biology 173-179 (1999).
X. Gallet et al., A Fast Method to Predict Protein Interaction Sites from Sequences, 302 J. Mol. Biol. 917-926 (2000).
D.A. Phoenix et al., The Hydrophobic Moment and Its Use In The Classification of Amphiphilic Structures (Review), 19 Molecular Membrane Biology 1-10 (2002).
H. Zhou et al., The Stability Scale and Atomic Solvation Parameters Extracted From 1023 Mutation Experiments, 49 Proteins: Struc. Funct. & Genetics 483-492 (2002).

\* cited by examiner

*Primary Examiner* — Eric S Dejong
(74) *Attorney, Agent, or Firm* — Ryan, Mason & Lewis, LLP

(57) ABSTRACT

Techniques for protein structure analysis are provided. In one aspect, an apparatus for characterizing a multi-domain protein structure comprises the following steps. For at least one domain, a hydrophobic dipole, e.g., defined as a first-order hydrophobic moment of the domain, is calculated. A score representing the orientation of the hydrophobic dipole of the at least one domain relative to a hydrophobic dipole of one or more other domains of the multi-domain protein structure is then calculated.

18 Claims, 9 Drawing Sheets

NEUMAIER HYDROPHOBICITY SCALE

| AMINO ACID | HYDROPHOBICITY | AMINO ACID | HYDROPHOBICITY |
|---|---|---|---|
| LYS | −1.00 | HIS | −0.15 |
| ASP | −0.97 | ALA | −0.06 |
| GLU | −0.85 | TYR | 0.35 |
| ARG | −0.80 | CYS | 0.56 |
| GLN | −0.71 | TRP | 0.57 |
| ASN | −0.70 | MET | 0.68 |
| SER | −0.48 | VAL | 0.75 |
| PRO | −0.45 | LEU | 0.83 |
| THR | −0.38 | PHE | 0.99 |
| GLY | −0.32 | ILE | 1.00 |

HYDROPHOBIC MOMENT OF MULTI-DOMAIN PROTEINS

CROSS REFERENCE TO RELATED APPLICATIONS

This application is a divisional application under 37 CFR §1.53(b) of U.S. application Ser. No. 10/921,493 filed Aug. 19, 2004, incorporated by reference herein.

FIELD OF THE INVENTION

The present invention relates to proteins and, more particularly, to techniques for analyzing protein structures.

BACKGROUND OF THE INVENTION

Proteins are composed of a series of amino acid residues. There are 20 naturally occurring amino acid residues. The three-dimensional structure of a protein typically comprises a series of folded regions. When predicting the structure of a protein, researchers attempt to determine the amino acid spatial order and location in three-dimensional space. Obtaining the three-dimensional structure of a protein is important because protein function depends upon the particular protein structure.

Understanding multi-domain protein folding is a current focus in protein science that remains a great challenge for researchers. For example, little, if anything, is known about how domain sequence boundaries are determined, how each individual domain folds (e.g., independently or cooperatively) or how domains assemble after each individual domains is formed. See, for example, R. Jaenicke, *Stability and Folding of Domain Proteins,* 71 PROG. BIOPHYS. & MOL. BIOL. 155-241 (1999); C. Anselmi, et al., *Identification of Protein Domains on Topological Basis,* 58 BIOPOLYMERS 218-229 (2001); S. J. Wheelan et al., *Domain Size Distributions Can Predict Domain Boundaries,* 16 BIOINFORMATICS 613-618 (2000); A. G. Murzin et al., *SCOP: A Structural Classification of Protein Database for the Investigation of Sequences and Structures,* 247 J. MOL. BIOL. 536-540 (1995), the disclosures of which are incorporated by reference herein.

Therefore, techniques would be desirable that allow for the analysis and elucidation of protein structures, including those having multiple domains.

SUMMARY OF THE INVENTION

The present invention provides techniques for protein structure analysis. In one aspect of the invention, an apparatus for analyzing a multi-domain protein structure comprises the following steps. For at least one domain, a hydrophobic dipole, e.g., defined as a first-order hydrophobic moment of the domain, is calculated. A score representing the orientation of the hydrophobic dipole of the at least one domain relative to a hydrophobic dipole of one or more other domains of the multi-domain protein structure is then calculated.

A more complete understanding of the present invention, as well as further features and advantages of the present invention, will be obtained by reference to the following detailed description and drawings.

DETAILED DESCRIPTION OF PREFERRED EMBODIMENTS

Figure 1:
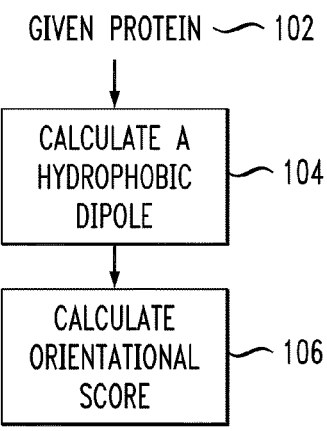
FIG. 1 is a diagram illustrating an exemplary methodology for analyzing a multi-domain protein structure according to an embodiment of the present invention.

FIG. 1 is a diagram illustrating an exemplary methodology for analyzing a multi-domain protein structure. Namely, in step 102 of FIG. 1, a multi-domain protein structure is provided for characterization. Suitable protein structures include, but are not limited to, native protein structures, engineered protein structures, e.g., those engineered to resemble native protein structures, or both native and engineered protein structures. Therefore, the techniques presented herein may be used to analyze engineered protein structures, e.g., to determine how closely they resemble native protein conformations. For example, some or all of the protein database (PDB) structures may be analyzed according to the present techniques to see the distribution of the orientational score defined below for all native multi-domain protein structures.

Further, according to the teachings presented herein, the multi-domain protein structure may comprise two or more domains. For example, as will be described in detail below, an exemplary multi-domain protein structure may comprise two domains.

In step 104 of FIG. 1, a hydrophobic dipole for each of the domains is calculated. As will be described in detail below, the hydrophobic dipole represents a first-order hydrophobic moment for the domain and may be calculated using an ellipsoidal representation of the domain.

In step 106 of FIG. 1, an orientational score is calculated using the hydrophobic dipoles calculated in step 104, above. Namely, the orientational score represents the orientation of the hydrophobic dipole of a domain relative to one or more other domains. As will be described in detail below, the orientational score may be defined, in part, by the angles between the hydrophobic dipoles and a vector common to one or more of the domains, e.g., based on the relative orientation of the hydrophobic dipoles, to capture the bias in domain hydrophobic dipole orientations.

Figure 2:
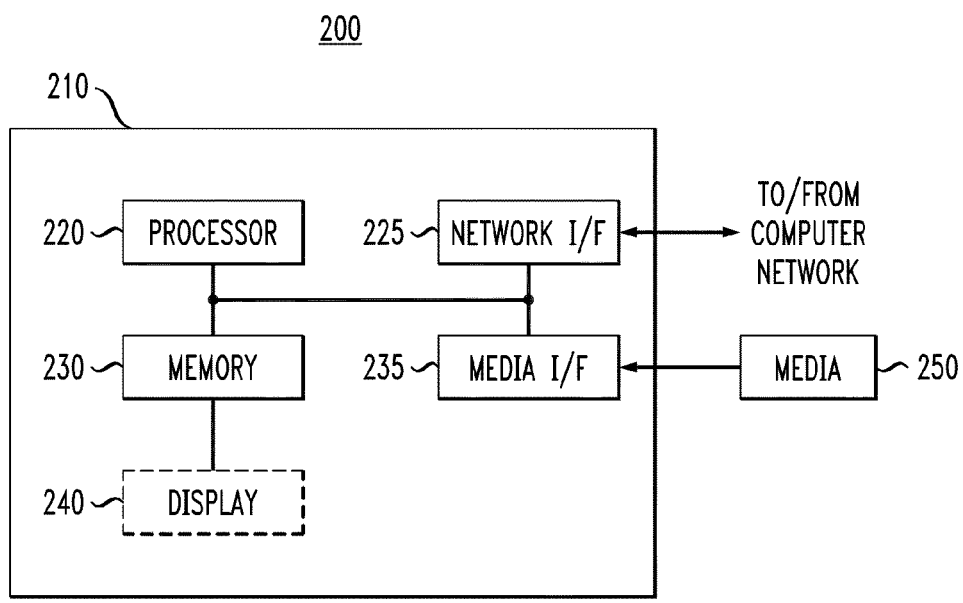
FIG. 2 is a diagram illustrating an exemplary system for analyzing a multi-domain protein structure according to an embodiment of the present invention.

FIG. 2 is a diagram illustrating an exemplary system for analyzing a multi-domain protein structure. Apparatus 200 comprises a computer system 210 that interacts with media 250. Computer system 210 comprises a processor 220, a network interface 225, a memory 230, a media interface 235 and an optional display 240. Network interface 225 allows computer system 210 to connect to a network, while media interface 235 allows computer system 210 to interact with media 250, such as a Digital Versatile Disk (DVD) or a hard drive.

As is known in the art, the methods and apparatus discussed herein may be distributed as an article of manufacture that itself comprises a computer-readable medium having computer-readable code means embodied thereon. The computer-readable program code means is operable, in conjunction with a computer system such as computer system 210, to carry out all or some of the steps to perform one or more of the methods or create the apparatus discussed herein. For example, the computer-readable code is configured to implement a method of analyzing a multi-domain protein structure by the steps of: for at least one domain, calculating a hydrophobic dipole; and calculating a score representing the orientation of the hydrophobic dipole of the at least one domain relative to a hydrophobic dipole of one or more other domains of the multi-domain protein structure. The computer-readable medium may be a recordable medium (e.g., floppy disks, hard drive, optical disks such as a DVD, or memory cards) or may be a transmission medium (e.g., a network comprising fiber-optics, the world-wide web, cables, or a wireless channel using time-division multiple access, code-division multiple access, or other radio-frequency channel). Any medium known or developed that can store information suitable for use with a computer system may be used. The computer-readable code means is any mechanism for allowing a computer to read instructions and data, such as magnetic variations on a magnetic medium or height variations on the surface of a compact disk.

Memory 230 configures the processor 220 to implement the methods, steps, and functions disclosed herein. The memory 230 could be distributed or local and the processor 220 could be distributed or singular. The memory 230 could be implemented as an electrical, magnetic or optical memory, or any combination of these or other types of storage devices. Moreover, the term "memory" should be construed broadly enough to encompass any information able to be read from or written to an address in the addressable space accessed by processor 220. With this definition, information on a network, accessible through network interface 225, is still within memory 230 because the processor 220 can retrieve the information from the network. It should be noted that each distributed processor that makes up processor 220 generally contains its own addressable memory space. It should also be noted that some or all of computer system 210 can be incorporated into an application-specific or general-use integrated circuit.

Optional video display 240 is any type of video display suitable for interacting with a human user of apparatus 200. Generally, video display 240 is a computer monitor or other similar video display.

Protein domains have generally been hypothesized to demarcate compact units that fold independently. This hypothesis suggests that the distribution of amino acid residue hydrophobicity for individual domains, as well as the distribution of hydrophobicity of the aggregate set of domains, should exhibit special properties. If domains do fold independently within an aqueous environment, it is expected that individual domains will exhibit a core composed predominantly of hydrophobic amino acid residues with an exterior composed predominantly of hydrophilic amino acid residues. Furthermore, as a consequence of domain coalescence within the aqueous environment it is expected that the amphiphilicity of spatially adjacent domains will reveal a bias of hydrophobic amino acid residues in the region of domain contact.

According to the teachings presented herein, hydrophobic spatial profiling for all single-chain multi-domain proteins in the PDB will be examined to illustrate biases in the hydrophobicity distribution. Namely, both the individual domains and the aggregate complexes of domains on a single chain will be profiled. As will be described in detail below, this is achieved, not only by examining the zero-order and second-order moment distributions of domain hydrophobicity, but also by the calculation of first-order moment orientations inside multi-domain protein structures. Hydrophobic protein profiling is described generally, for example, in B. D. Silverman, *Hydrophobic Moments of Protein Structures: Spatially Profiling the Distribution,* 98 Proc. Natl. Acad. Sci. USA 4996-5001 (2001) (hereinafter "Silverman"); R. Zhou et al., *Spatial Profiling of Protein Hydrophobicity: Native vs. Decoy Structures,* 52 Proteins: Struc. Funct. & Genetics 561-572 (2003) (hereinafter "Zhou"), the disclosures of which are incorporated by reference herein.

Moments of a set of values distributed in space can help condense the information provided by the distribution. See Silverman and Zhou. For example, the hydrophobic helical moment, a vector with amplitude and direction, provides a measure of the amphiphilicity of a helix perpendicular to the helical axis. See, for example, D. Eisenberg et al., *The Helical Hydrophobic Moment: A Measure of the Amphiphilicity of a Helix,* 299 Nature 371-374 (1982) (hereinafter "Eisenberg"), the disclosure of which is incorporated by reference herein.

Such first-order measure of hydrophobic imbalance, dependent upon the spatial distribution of the values of amino acid hydrophobicity, has been useful in connection with cell surface binding affinity and helical function studies. See for example, D. Eisenberg et al., *Analysis of Membrane Protein Sequences with the Hydrophobic Moment Plot,* 179 J. Mol. Biol. 125-142 (1984); H. J. Pownall et al., *Helical Amphipathic Moment: Application to Plasma Lipoproteins,* 159 FEBS 17-23 (1983); I. Tsigelny et al., *Mechanism of Action of Chromogranin A On Catecholamine Release: Molecular Modeling of the Catestatin Region Reveals a β-strand/loop/β-strand Structure Secured by Hydrophobic Interactions and Predictive of Activity,* 77 Regulatory Peptides 43-53 (1998); J. P. Pardo et al., *An Alternative Model for the Transmembrane Segments of the Yeast H+–ATPase,* 15 YEAST 1585-1593 (1999); P. W. Mobley et al., *Membrane Interactions of the Synthetic N-Terminal Peptide of HIV-1 gp41 and Its Structural Analogs,* 1418 Biochimica Et Biophysica Acta 1-18 (1999); L. Thong et al., *Flexible Programs for the Prediction of Average Amphiphilicity of Multiply Aligned Homologous Proteins: Application to Integral Membrane Transport Proteins,* 16 Molecular Membrane Biology 173-179 (1999); X. Gallet et al., *A Fast Method to Predict Protein Interaction Sites from Sequences,* 302 J. Mol. Biol. 917-926 (2000) and D. A. Phoenix et al., *The Hydrophobic Moment and Its Use In The Classification of Amphiphilic Structures (Review),* 19 Molecular Membrane Biology 1-10 (2002), the disclosures of which are incorporated by reference herein.

As will be described in detail below, the first order moment of a molecular charge distribution, the molecular dipole moment, is a quantity that provides the major fraction of the electrostatic interaction energy between molecules in space. The hydrophobic moments of a protein structure may be used to develop a linear first-order hydrophobic moment (referred to hereafter as the "hydrophobic dipole"), analogous to the dipole moment, for the entire tertiary protein structure which yields a dual measure comprised of the degree and direction of protein hydrophobic imbalance or amphiphilicity.

With a measure such as the hydrophobic dipole, defined above, a simple comparison of the amphiphilicity of different protein structures can be made. For example, two protein structures with the same fold and close in root mean square deviation (RMSD) might exhibit very different degrees of overall hydrophobic organization. Such differences in the degrees of hydrophobic organization would be concisely summarized by the global linear hydrophobic moment. The direction of the hydrophobic dipole may also assist in identifying regions of functional interest.

Furthermore, as will be described in detail below, a scoring function based on the relative orientation of the hydrophobic dipole can be defined so as to measure the bias in the domain hydrophobic dipole orientations within multi-domain complexes. Such an orientational scoring function reveals that up to 80 percent of multi-domain complexes are in favor of the hydrophobic dipoles pointing towards each other which provides an explanation as to the well-defined second-order hydrophobic moment profiles for multi-domain complexes (since a simple addition of the two or more well-defined hydrophobic profiles of individual domains do not necessarily yield a native-like profile for the complex). It is this orientational bias that provides a mechanism for the multi-domain proteins to have a native-like hydrophobic spatial profile.

Hydrophobicity is widely used to describe the salvation of small organic molecules, proteins, or other such molecules in a water solvent. For proteins, each amino acid residue making up the protein exhibits a different degree of hydrophobicity (or hydrophilicity) based upon the solubility of that amino acid in water. A value of hydrophobicity $h_i$ can then be assigned to each amino acid residue of type i.

Figures 3, 4A:
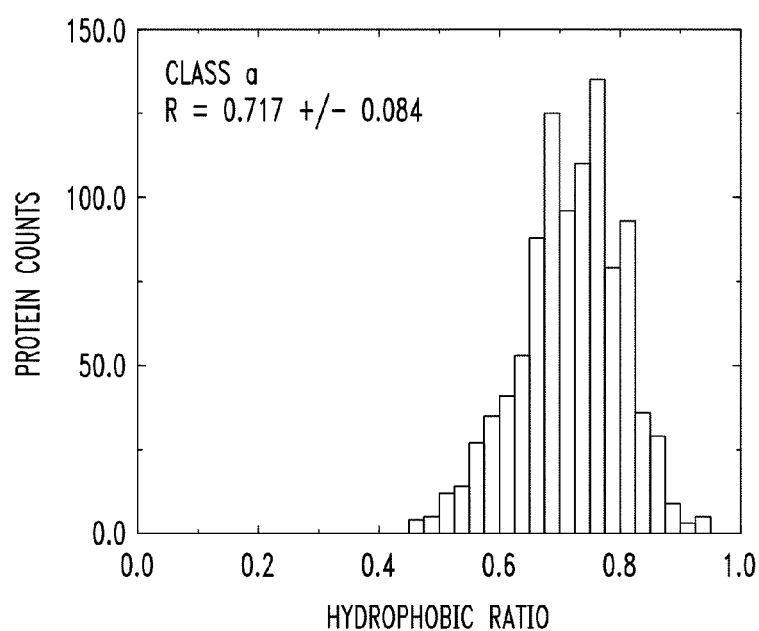
FIG. 3 is a chart illustrating the Neumaier hydrophobicity scale values for each of the 20 naturally occurring amino acid residues.
FIGS. 4A-E are graphs illustrating the hydrophobic ratio for domains in the structural classification of protein (SCOP) database, classes a through e, which are globular soluble proteins according to an embodiment of the present invention.
Figure 4B:
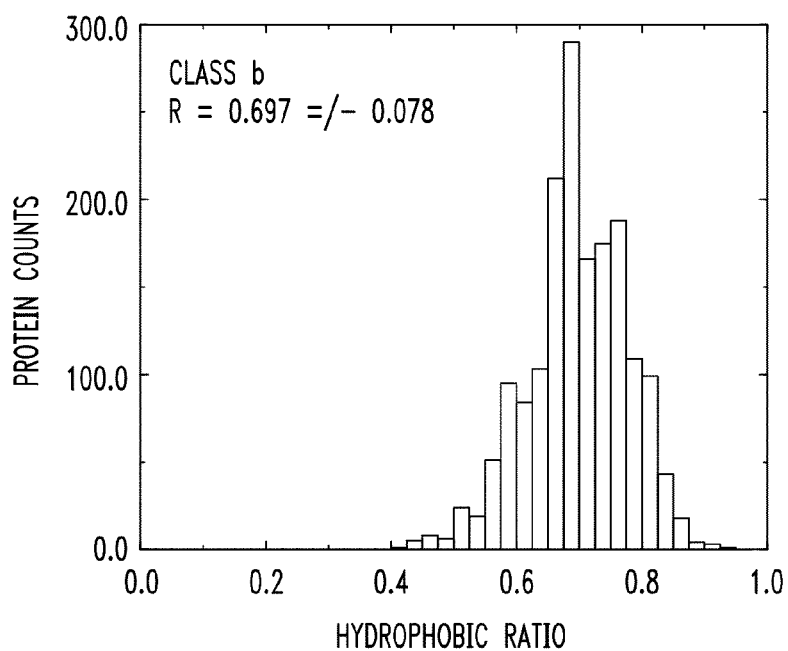
Figure 4C:
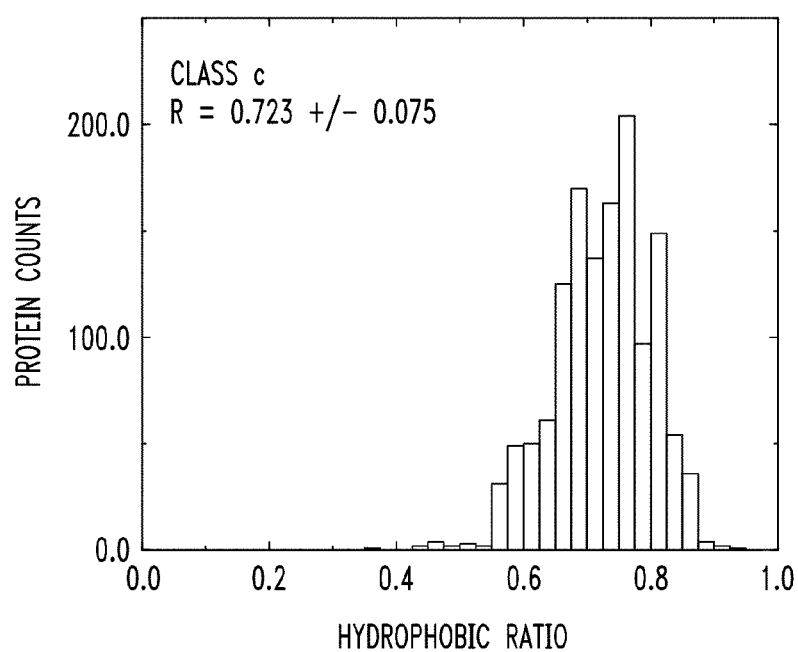
Figure 4D:
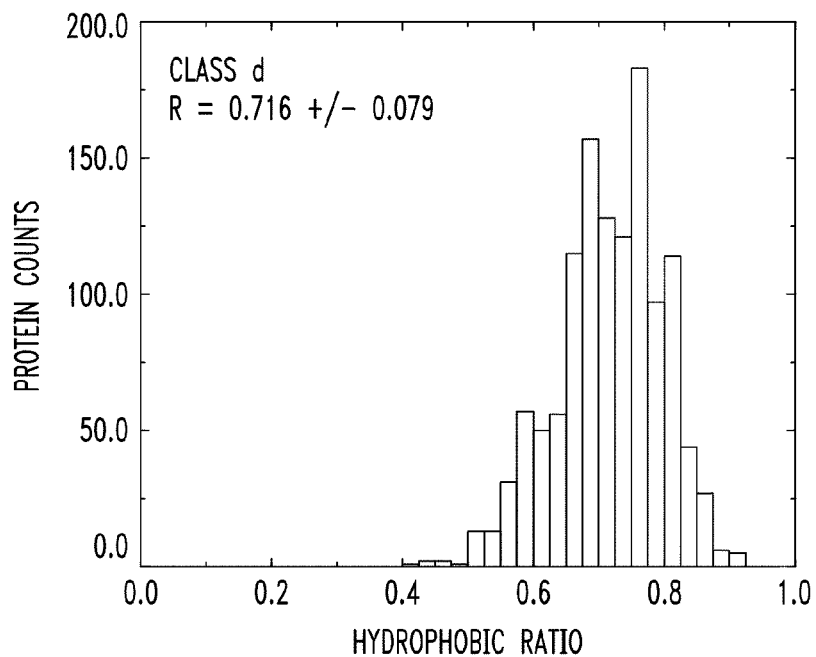
Figure 4E:
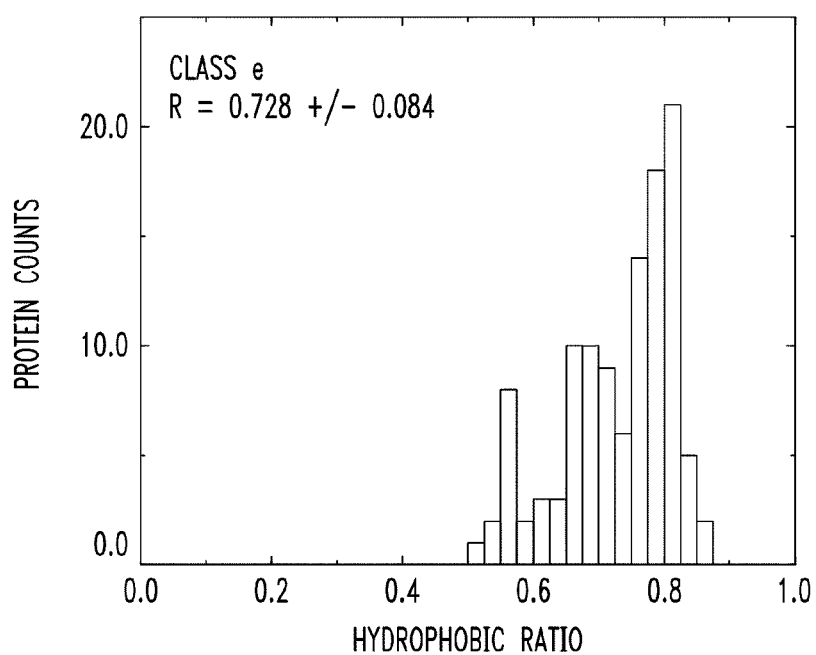

FIG. 3 is a chart illustrating Neumaier hydrophobicity scale values for each of the naturally occurring amino acid residues, with hydrophobic amino acid residues having a positive hydrophobicity and hydrophilic amino acid residues having a negative hydrophobicity. While the present techniques are described based upon the Neumaier hydrophobicity scale, it is to be understood that use of this particular scale is only exemplary and any other suitable hydrophobicity scale may be employed. Other suitable hydrophobicity scales include, but are not limited to, the Eisenberg scale (see, for example, Eisenberg) and the Zhou scale (see, for example, H. Zhou et al., *The Stability Scale and Atomic Solvation Parameters Extracted From* 1023 *Mutation Experiments,* 49 PROTEINS: STRUC. FUNCT. & GENETICS 483-492 (2002), the disclosure of which is incorporated by reference herein).

The present calculations are based upon the amino acid residue side-chain locations of the protein. The center-of-geometry of the i th amino acid residue, or amino acid residue centroid $\vec{r}_i$ is calculated based on all side chain atoms of that amino acid residue. This distribution of points in three-dimensional space enables calculation of the geometric center $\vec{r}_c$, namely, the centroid of the side-chain centroids of the protein structure:

$$\vec{r}_c = \frac{1}{n}\sum_i \vec{r}_i, \quad \{1\}$$

wherein n is the total number of amino acid residues.

Linear hydrophobic imbalance about the average value of protein hydrophobicity $\bar{h}$ is given by the following first-order hydrophobic moment, or hydrophobic dipole:

$$\vec{H}_1 = \frac{1}{n}\sum_i (h_i - \bar{h})\vec{r}_i, \quad \{2\}$$

wherein $\vec{H}_1$ is invariant with respect to the choice of the origin of the moment expansion, since the subtraction of the mean of the distribution $\bar{h}$ yields a distribution, $(h_i-\bar{h})$, with vanishing zero-order moment. As such, Equation 2, above, can be rewritten as:

$$\vec{H}_1 = \frac{1}{n}\sum_i h_i(\vec{r}_i - \vec{r}_c). \quad \{3\}$$

The first-order hydrophobic imbalance about the mean value of hydrophobicity is, therefore, given by the global linear hydrophobic moment calculated with the centroid of amino acid residue side chains as the origin. Identification of the spatial origin of the moment expansion enables explicit registration of the moment vector with the protein structure.

The distribution of hydrophobicity is profiled from the interior to the exterior of globular proteins, and an ellipsoidal profiling shape may be chosen with axes determined by the moments of geometry of the amino acid residue distribution. See, for example, Silverman and Zhou. The ellipsoidal representation is generated from the molecular moments-of-inertia tensor I which has elements, $$I_{jk}=\int\rho(\vec{r})(r^2\delta_{jk}-x_jx_k)dV, \quad \{4\}$$

wherein $\rho(\vec{r})$ is the density of amino acid residue centroids of unit mass, $\delta_{jk}$ is the Kronecker delta function with a value of one if j=k, and zero otherwise.

Diagonalizing the moment-of-inertia matrix, one obtains the three principal axes as well as the moments of geometry. The x, y and z axes are then aligned with the principal axes. The moments of geometry are designated as $g_1$, $g_2$ and $g_3$, with $g_1<g_2<g_3$. The ellipsoidal representation generated by these moments can then be written as, $$x^2+g_2'y^2+g_3'z^2=d^2, \quad \{5\}$$

wherein $g_2'=g_2/g_1$, $g_3'=g_3/g$ . The value d is the major principal axis of the ellipsoid and can be considered as a generalized ellipsoidal radius.

Using the above ellipsoidal representation, the second-order and zero-order hydrophobic moments can be defined, since, as will be described in detail below, they will be used for comparison between single domains and multi-domain complexes. The zero-order hydrophobic moment can be easily obtained by accumulating the amino acid residues within the ellipsoidal distance d, $$H_0(d) = \sum_{r<d} h_i'. \quad \{6\}$$

The prime designates the hydrophobicity values of each amino acid residue after normalization (mean zero with standard deviation of one) to allow for comparison across various proteins. When the value of d is just sufficiently large enough to collect all of the amino acid residues, the net hydrophobicity of the protein vanishes. This value of $d_0$, for which $H_0(d)$ vanishes, assigns a surface as common structural reference for each protein structure.

Second-order moments amplify the differences between hydrophobic and hydrophilic amino acid residues that contribute to the spatial profile of the hydrophobicity distribution. The second-order hydrophobic moment is defined as, $$H_2(d) = \sum_{r<d} h'_i(x_i^2 + g'_2 y_i^2 + g'_3 z_i^2) \quad \{7\}$$

wherein the $(x_i, y_i, z_i)$ denote the position of an amino acid residue centroid. For globular, soluble protein structures, the zero- and second-order moments are mostly positive when d is small. Both moments increase with distance d within the region of the hydrophobic core of the protein structure. As the values of d increase, the ratio of hydrophilic to hydrophobic amino acid residues increases. The increase of both the zero- and second-order moments with d eventually slows and then begins to decrease with increasing d. For example, as will be described below, individual domains are found to exhibit well-defined second-order hydrophobic moment profiles with a solid hydrophobic core peak and a sharp hydrophilic protein exterior plunge.

Since the second-order moment amplifies differences in the distribution, this moment will cross zero, becoming negative at a distance below the value of $d_0$, the location at which the zero-order moment vanishes. This location at which the second-order moment vanishes is defined as $d_2$. The hydrophobic-ratio is then defined as, $$R_H = d_2/d_0 \quad \{8\}$$

$R_H$ is a relatively constant, 0.71±0.08, for all native globular soluble protein domains. See, for example, Zhou. The profiles of multi-domain proteins will be addressed herein.

Similar to the second-order moment calculations, the first-order moment, or hydrophobic dipole as in Equation 3 above, can be modified by including the effect of lever arm dependence. For example, an amino acid residue near the exterior of the protein structure and also near a major principal axis is at a greater distance from the center of the protein than an amino acid residue near the exterior of the protein structure but proximate to a minor principal axis, however, their contribution to hydrophobic contact might be similar. Even though two amino acid residues at different locations on the same ellipsoid have the same fractional distance to the protein surface, their distances from the origin can be very different. These two amino acids would, therefore, make different contributions to the magnitude of the vector, $\vec{r}_i$, present in Equation 3, above. This difference in contributions can be corrected by mapping the ellipsoidal coordinates onto a sphere with a radius equal to the major principal axis. With this mapping, Equation 3 becomes:

$$\vec{H}_1 = \frac{1}{n} \sum_i h_i(x_i \hat{i} + \sqrt{g'_2}\, y_i \hat{j} + \sqrt{g'_3}\, z_i \hat{k} - \vec{r}_c). \quad \{9\}$$

The $\hat{i}, \hat{j}, \hat{k}$ are unit vectors along the directions of the principal axes. Since Equation 9 is written in the frame of the principal axes, $\vec{r}_c$ is at the origin and does not shift with the mapping.

The mapping places all amino acid residues on the same ellipsoid surface at the same distance from the center of the protein structure. It correlates more closely with amino acid residue solvent accessibility than the amino acid residue distance from the ellipsoidal center prior to the mapping.

For multi-domain proteins, it is of great interest to know how the individual domains assemble together once each domain is formed. As mentioned above, if domains do fold independently within an aqueous environment, it is expected that, as a consequence of domain coalescence, the amphiphilicity of spatially adjacent domains will reveal a bias of the hydrophobic dipole orientation. Thus, an orientational score $f(\theta)$ is defined to catch this orientation bias. For example, for a two-domain protein, $f(\theta)$ is $$\cos(\theta_1) = \frac{(\vec{H}_1 \cdot \vec{r}_{12})}{|\vec{H}_1||\vec{r}_{12}|} \quad \{10\}$$

$$\cos(\theta_2) = \frac{(\vec{H}_2 \cdot \vec{r}_{21})}{|\vec{H}_2||\vec{r}_{21}|}$$

$$f(\theta) = \frac{1}{2}(\cos(\theta_1) + \cos(\theta_2))$$

wherein $\vec{r}_{12}$ is the vector between the two domain centers, $\theta_1$ and $\theta_2$ are the angles between the hydrophobic dipoles, $\vec{H}_1$ and $\vec{H}_2$, and the inter-domain distance vectors, respectively. The angles between the hydrophobic dipoles and the inter-domain distance vectors will be described in detail below, for example, in conjunction with the description of FIGS. 6A-B. For protein structures having more than two domains, $f(\theta)$ is determined by averaging over $f(\theta)$ values from some or all possible combinations of two domains (total $C_m^2$ combinations for m-domains).

Globular soluble proteins were extracted from the protein database (PDB). Procedures for obtaining globular soluble proteins are described, for example, in Zhou. Namely, the conflicts in amino acid residue sequences in SEQRES, PDB records related to the amino acid sequence of the protein, and ATOM, PDB records related to the sequence of atoms observed in the protein, are first resolved for each protein chain, resulting in a total of 30,856 chains (some proteins have multiple chains). Structural classification of protein (SCOP) database (version 1.53) is then used to identify soluble globular protein domains (e.g., classes a through e). The domain definition in SCOP is then mapped onto the amino acid residue ranges in the PDB chains.

A non-redundant subset of domain length protein sequences is obtained through a pair-wise sequence alignment process that retains domains that have sequence identities below 95 percent. This procedure yields a total of 5,786 soluble globular protein domains. After introducing a protein size limit (e.g., only those proteins with greater than 70 amino acid residues were selected) in order to get smooth hydrophobic moment profiles with meaningful statistics, a total of 5,387 protein domains were obtained.

As mentioned above, $R_H$ is a relatively constant, 0.71±0.08, for all native globular soluble protein domains, as is the case for this large set of non-redundant soluble globular proteins. The present techniques will be applied to the protein domains in each SCOP class, e.g., classes a through e (as mentioned above). FIGS. 4A-E are graphs illustrating the hydrophobic ratio for domains in the SCOP database, classes a through e, which are globular soluble proteins, e.g., class a) all alpha-helix proteins; class b) all beta-strand proteins; class c) alpha-helix plus beta-strand proteins; class d) alpha-helix and beta-strand proteins (a/b); class e) multi-domain proteins.

All of the above classes show a well-defined relative constant hydrophobic ratio near 0.72. Namely, the hydrophobic ratios were found to be 0.72±0.08, 0.70±0.08, 0.72±0.08, 0.72±0.08 and 0.73±0.08, for classes a-e, respectively. Thus, the relative constant hydrophobic ratio holds well for each of these SCOP classes with native protein-like distributions. The only distribution that shows some deviation is highlighted by the graph of class e, shown illustrated in FIG. 4E. This distribution, namely that of the multi-domain proteins, may exhibit some deviation because with multi-domain proteins, there are some hydrophobic amino acid residues distributed near the domain surface to make hydrophobic contacts with adjacent domains (as will be discussed in detail below). Thus, the hydrophobic ratio will be slightly larger for these domains since some of the hydrophobic amino acid residues are shifted towards the exterior.

Multi-domain protein complexes are then analyzed to determine whether they may be profiled well as a whole. In other words, given that each individual domain can be profiled well as native-like (see, for example, Zhou), the next step is to determine whether the complex of two or more domains can still be profiled native-like. To investigate profiling a complex of two or more domains, all single-chain, multi-domain proteins were selected out of the above classes a through e (e.g., some proteins in classes a through d have multiple domains as well, but the SCOP database classifies them as being one of class a through d rather than of class e). Multi-chain domains are not included, to avoid complexity. As such, a total of 162 chains and 358 domains, with an average of 2.2 domains per chain resulted.

Figure 5A:
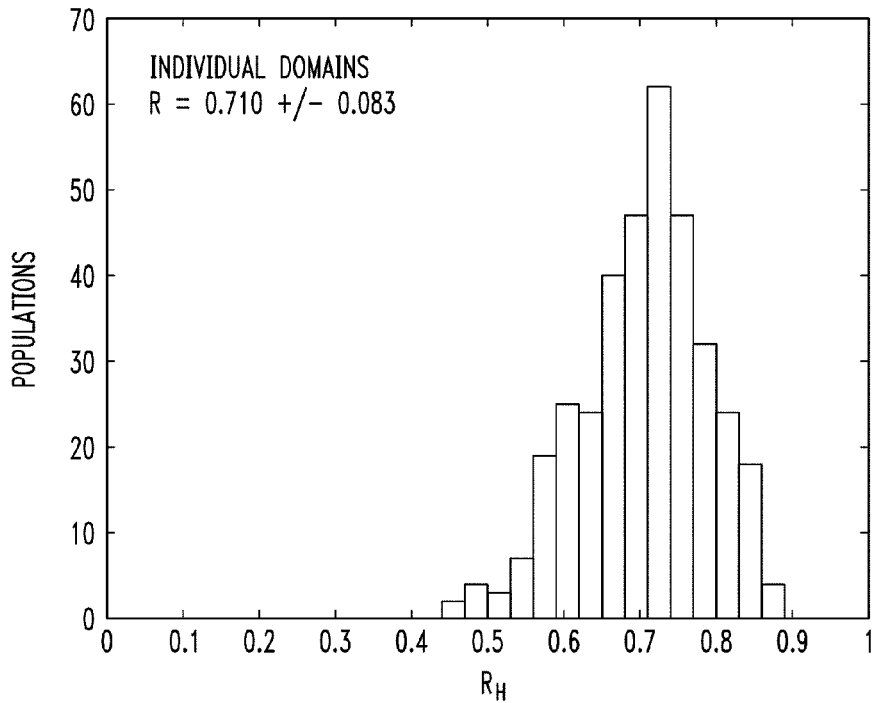
FIGS. 5A-B are graphs illustrating the hydrophobic ratio distribution for multi-domain proteins in a single chain according to an embodiment of the present invention.
Figure 5B:
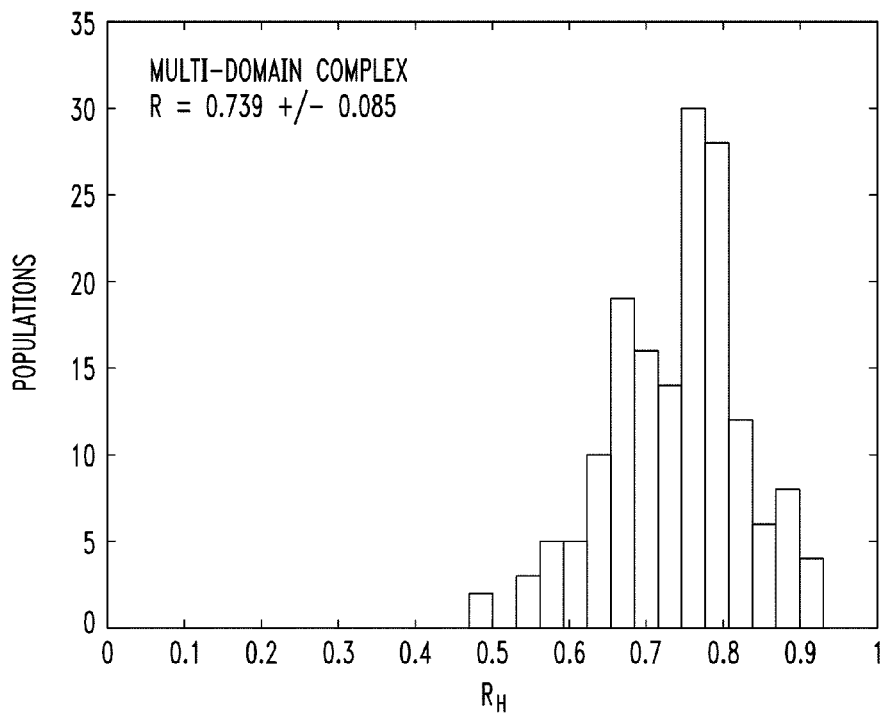

It was found that these single chains or multi-domain complexes profiled with a well-defined hydrophobic ratio $R_h$. FIGS. 5A-B are graphs illustrating the hydrophobic ratio distribution for multi-domain proteins in a single chain. Namely, FIG. 5A is a graph illustrating the hydrophobic ratio distribution for multi-domain proteins in a single chain for individual domains. FIG. 5B is a graph illustrating the hydrophobic ratio distribution for multi-domain proteins in a single chain for the multi-domain complex. The hydrophobic ratio for individual domains is 0.71±0.08 (see FIG. 5A), while the ratio for the entire chain, e.g., multi-domain complexes having at least two domains, is 0.74±0.08 (see FIG. 5B). Therefore, the multi-domain complexes exhibit well-defined second-order moment profiles, with a hydrophobic ratio of 0.74±0.08 for all single-chain multi-domain proteins in the PDB, while the hydrophobic ratio for the corresponding individual domains is 0.71±0.08.

These results indicate that there must be some angular bias or orientation bias in the first-order hydrophobic moment of the individual domains making up these multi-domain proteins. Namely, there must be some amphiphilicity or hydrophobic imbalance inside individual domains of the multi-domain proteins. If domains were to fold independently of each other within an aqueous environment, it would be expected that each individual domain would exhibit a well-defined core composed predominantly of hydrophobic amino acid residues and an exterior composed predominantly of hydrophilic amino acid residues. However, this does not explain multi-domain assembly that would result in multi-domain protein structures with a native protein-like profile. As will be described below, there exists a strong bias in the orientational score, e.g., as compared to a random distribution, due to domain coalescence within the aqueous environment.

Figure 6A:
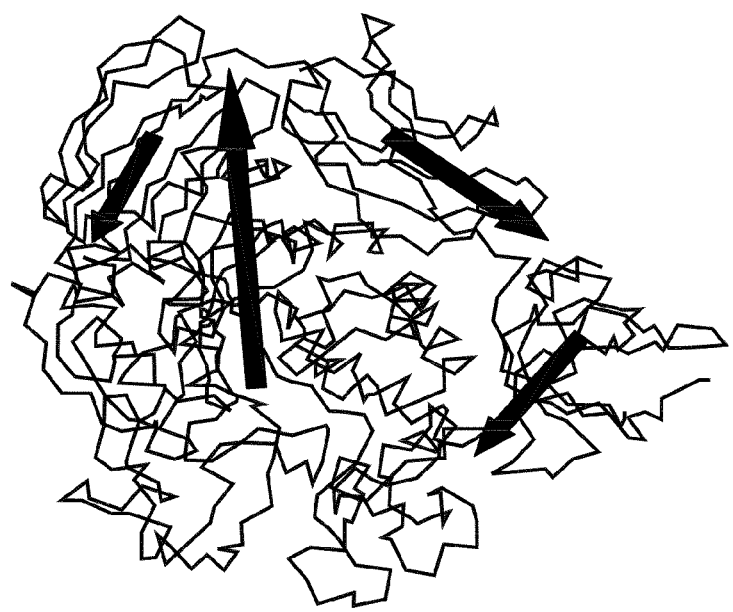
FIGS. 6A-B are ribbon diagrams illustrating exemplary multi-domain protein complexes with domain hydrophobic dipole orientations according to an embodiment of the present invention.
Figure 6B:
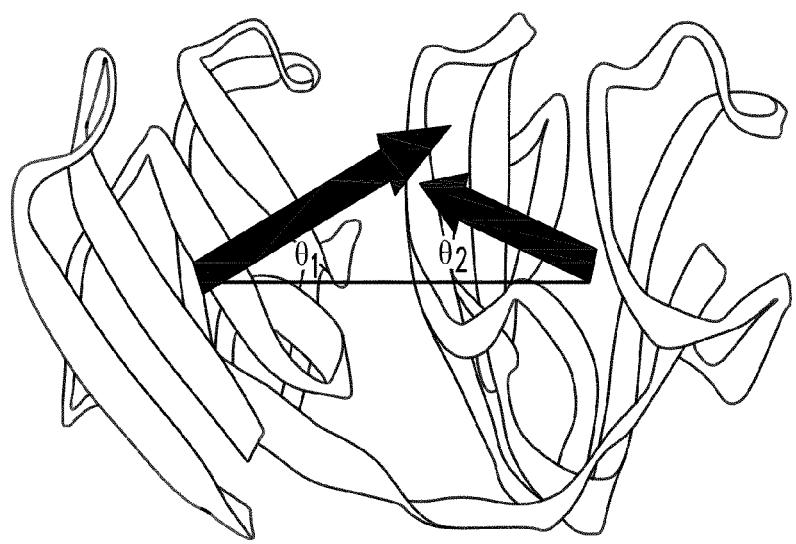

Thus, as a consequence of domain coalescence it is expected that there would exist a bias of hydrophobic amino acid residues in the region of domain contact, e.g., due to the amphiphilicity of spatially adjacent domains. Thus, the first-order moment of these domains are further computed to provide a concise measure of the degree and direction of the amphiphilicity or hydrophobic imbalance. FIGS. 6A-B are ribbon diagrams illustrating exemplary multi-domain protein complexes with domain hydrophobic dipole orientations. Namely, FIGS. 6A-B illustrate the first-order hydrophobic moment or hydrophobic dipole for the exemplary multi-domain complexes. Specifically, FIG. 6A illustrates an exemplary four domain protein structure and FIG. 6B illustrates an exemplary two domain protein structure. The magnitudes of the dipoles are represented by the length of the vectors. FIG. 6B also illustrates the angles used for the orientational score $f(\theta)$. The cosine of these angles, namely $\cos(\theta 1)$ and $\cos(\theta 2)$, are expected to have a tendency to be positive since the domain boundaries tend to have the more hydrophobic amino acid residues buried. FIG. 6B also shows that the hydrophobic dipoles have a tendency to point towards each other, which indicates a tendency of hydrophobic amino acid residues to group near the region(s) of domain contact.

The orientational score $f(\theta)$ is thus defined based on the relative orientation of the hydrophobic dipoles to capture the effect of hydrophobic amino acid residues grouping near the region(s) of domain contact, as described above. Therefore, the cosine of these angles, $\cos(\theta 1)$ and $\cos(\theta 2)$, is then expected to have a bias towards being more positive than negative.

Figure 7:
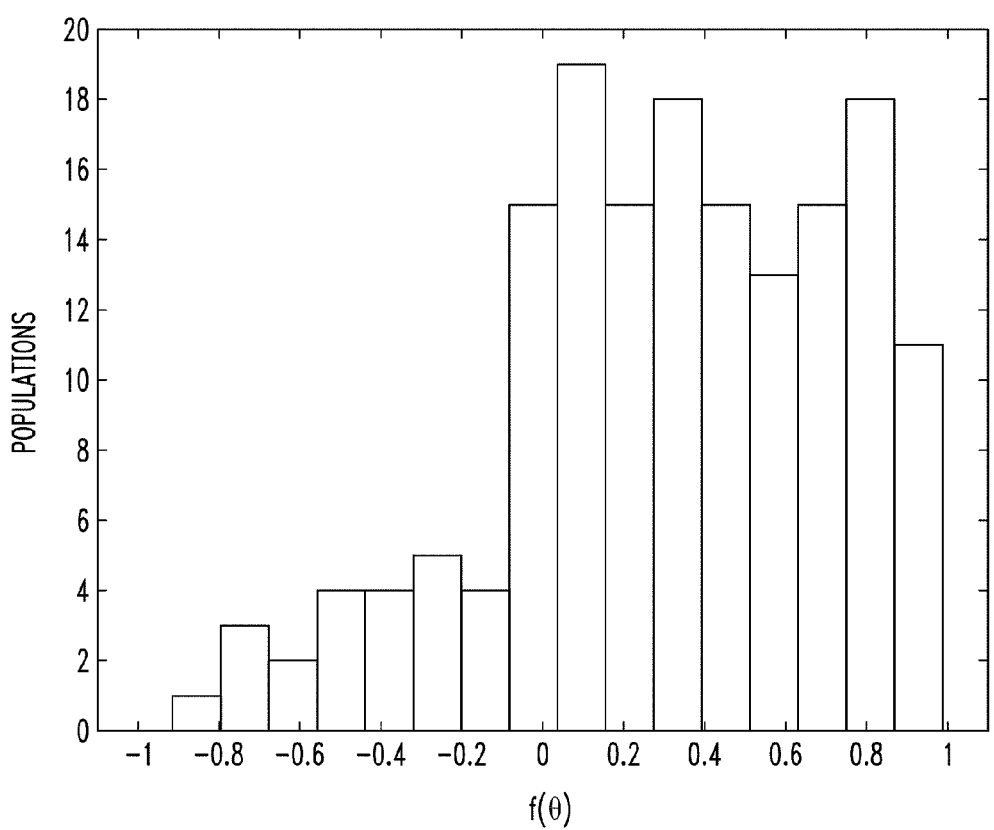
FIG. 7 is a graph illustrating the distribution of the function $f(\theta)$, which describes the relative orientation of individual domain hydrophobic dipoles according to an embodiment of the present invention.

FIG. 7 is a graph illustrating the distribution of the function $f(\theta)$, which describes the relative orientation of individual domain hydrophobic dipoles. If there is no bias, for randomly distributed domain dipoles, a mean value of $f(\theta)$ of zero should be expected, with about 50 percent of the $f(\theta)$ values less than zero and 50 percent of the $f(\theta)$ values greater than zero. The results, however, show that 79.4 percent of complexes have a $f(\theta)$ value greater than zero, with a mean of 0.32. Thus, it is clear that there exists a strong tendency for individual domains to re-orientate themselves to bury more hydrophobic amino acid residues or hydrophobic surface areas to the interior of the domain. This result provides an explanation as to the well-defined hydrophobic profiles and hydrophobic ratios for the multi-domain single-chain complexes.

The re-orientation of domain hydrophobic dipoles and burying of hydrophobic amino acid residues near the domain contact regions provides a means for the multi-domain protein to have a combined hydrophobic core. It also indicates that each individual domain in the complex not only arranges itself to have its own hydrophobic core, but also generates a hydrophobic imbalance or amphiphilicity to make the final assembled complex have a well-defined hydrophobic core in an aqueous environment.

Figure 8A:
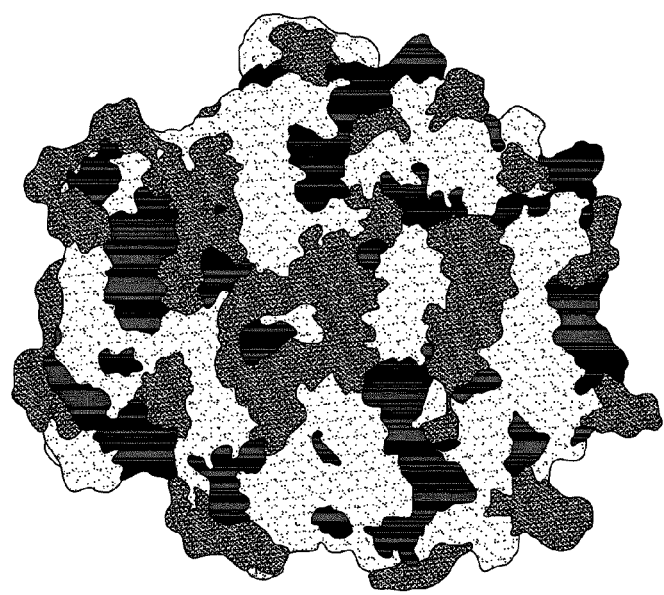
FIGS. 8A-C are diagrams illustrating the Connolly surface areas of hydrophobic and hydrophilic amino acid residues for an exemplary multi-domain protein.
Figure 8B:
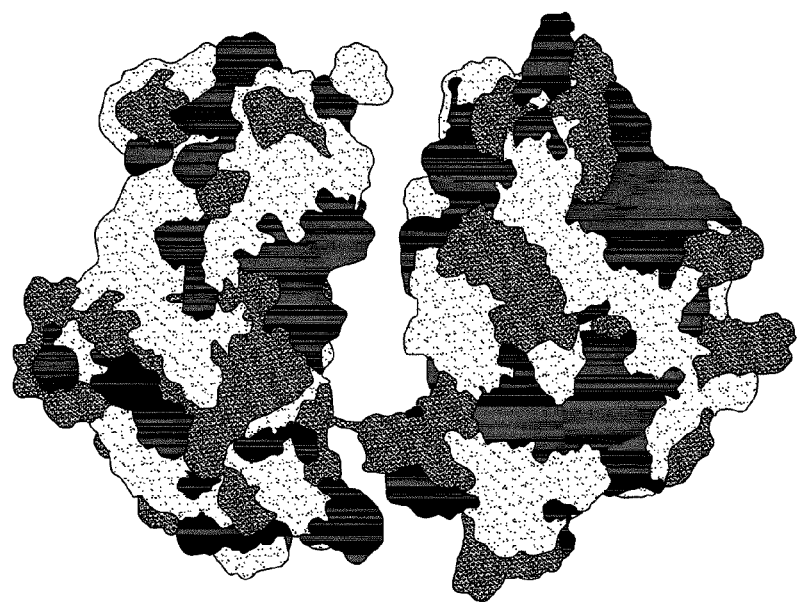
Figure 8C:
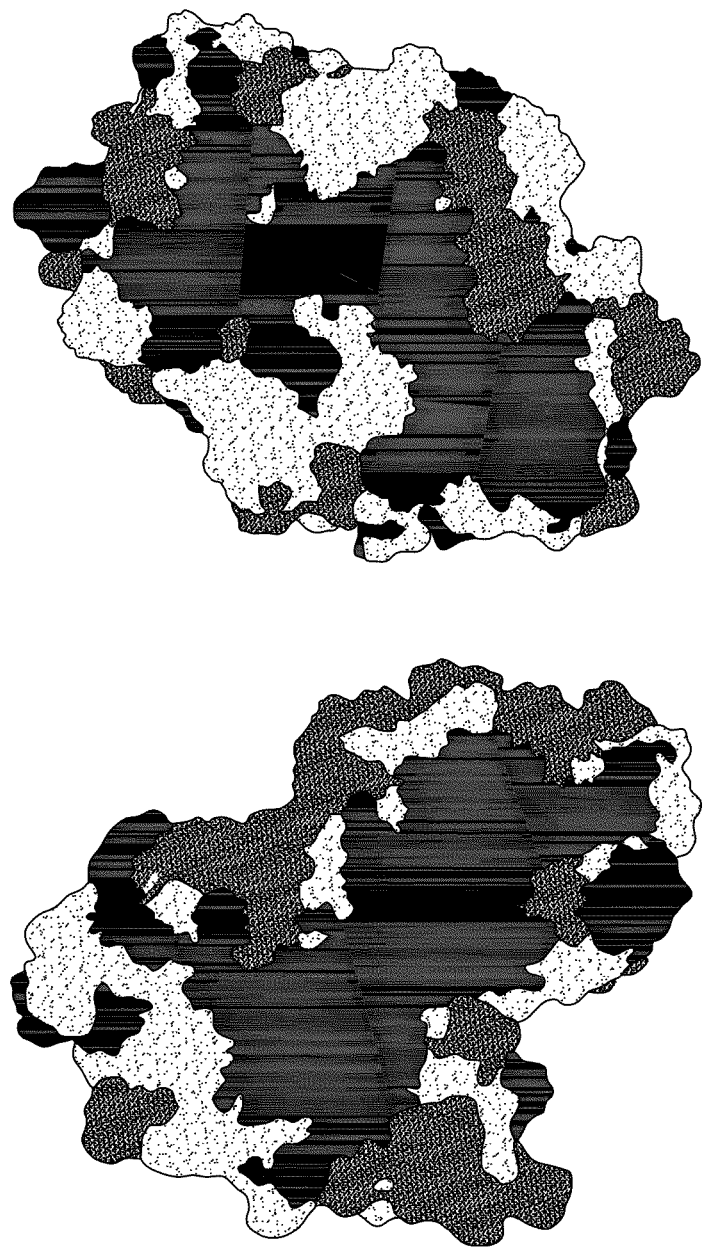

This orientation can be seen from hydrophobic surface area analysis. For example, FIGS. 8A-C are diagrams illustrating the Connolly surface areas of hydrophobic and hydrophilic amino acid residues for one exemplary multi-domain protein, 1dhy.pdb, which shows a large orientational score, e.g., $f(\theta)$ =0.84. The hydrophobic amino acid residues (e.g., I, F, V, M, W, C, Y), the strong hydrophilic amino acid residues (e.g., K, D, E, R, Q, N) and the weak hydrophilic amino acid residues are represented by dark, medium and light shading, respectively. FIGS. 8A-C show large hydrophobic surface areas near the domain boundary and strong orientational biases in the domain amphiphilicity or hydrophobic imbalance. They also show large hydrophilic surface areas on the other parts of the domain surface. Overall, there are more hydrophilic surface areas around the two domain surfaces, since each domain still needs to generate a stable hydrophobic profile in order to stay properly folded.

The hydrophobic surface areas, on the other hand, reside primarily near the domain boundary. This configuration will generate a strong orientational bias for the hydrophobic dipole, consistent with the above hydrophobic orientational score analysis.

Thus, this domain amphiphilicity or hydrophobic imbalance provides a characterization for multi-domain protein folding. First, each domain folds substantially independently into its own stable shape, which generates a native protein-like hydrophobic profile for each domain, and then the folded individual domains re-orientate themselves to bury, as much as is possible, the hydrophobic amino acid residues in the interior of the domain, in order to form the final complex having a stable final multi-domain structure.

As mentioned above, several different hydrophobicity scales may be employed in accordance with the present teachings, including, but not limited to, the Neumaier hydrophobicity scale, the Eisenberg scale and the Zhou scale. It is important to note that when the Neumaier scale is employed the results are slightly better, but the differences are very small. For example, the differences in the percentage of multi-domain proteins showing a larger than zero orientation score are only a few percentages. For most structure complexes the direction of the moment vector is relatively independent of the hydrophobicity scale chosen, since there is strong orientation bias in these multi-domain proteins. The effects, however, for single domain proteins may be greater. Namely, the effects in the magnitude and direction of the hydrophobic dipoles might be affected by the hydrophobicity scale chosen.

Although illustrative embodiments of the present invention have been described herein, it is to be understood that the invention is not limited to those precise embodiments, and that various other changes and modifications may be made by one skilled in the art without departing from the scope or spirit of the invention.

What is claimed is:

1. An apparatus for characterizing a multi-domain protein structure, the apparatus comprising:
    a memory; and
    at least one processor, coupled to the memory, operative to:
        for at least one domain, calculate a hydrophobic dipole, wherein calculating the hydrophobic dipole comprises referencing a structural feature of the at least one domain, and wherein calculating the hydrophobic dipole is carried out by a component executing on a hardware processor;
        calculate a score representing orientation of the hydrophobic dipole of the at least one domain relative to a hydrophobic dipole of one or more other domains of the multi-domain protein structure, wherein the score indicates an effect of one or more hydrophobic amino acid residues grouping near a region of domain contact, and wherein calculating the score is carried out by a component executing on a hardware processor;
        use the score to determine a bias in a domain hydrophobic dipole orientation within the multi-domain protein structure, and compare the score to a score of one or more native multi-domain protein structures to determine if the multi-domain protein structure resembles one or more native protein conformations, wherein determining a bias in a domain hydrophobic orientation comprises taking into account the calculated hydrophobic dipole of the at least one domain in the multi-domain protein structure, and wherein using the score to determine a bias in a domain hydrophobic dipole orientation within the multi-domain protein structure is carried out by a component executing on a hardware processor; and
        output the score representing orientation of the hydrophobic dipole of the at least one domain relative to a hydrophobic dipole of one or more other domains of the multi-domain protein structure to at least one of a user and a display.

2. The apparatus of claim 1, wherein the multi-domain protein structure comprises two domains.

3. The apparatus of claim 1, wherein the multi-domain protein structure comprises more than two domains.

4. The apparatus of claim 1, wherein the hydrophobic dipole comprises a first-order hydrophobic moment of the at least one domain.

5. The apparatus of claim 1, wherein the multi-domain protein structure comprises a single-chain multi-domain protein.

6. The apparatus of claim 1, wherein the multi-domain protein structure comprises an engineered protein structure.

7. The apparatus of claim 1, wherein an angle between the hydrophobic dipole and an inter-domain center-to-center distance vector common to the at least one domain and the one or more other domains is used to calculate the score.

8. The apparatus of claim 7, wherein the vector common to the at least one domain and the one or more other domains comprises an inter-domain distance vector.

9. The apparatus of claim 1, wherein the at least one processor, coupled to the memory, operative to calculate a score is further operative to calculate, for a two-domain protein, $f(\theta)$, wherein calculating $f(\theta)$ comprises calculating $$\cos(\theta_1) = (\vec{H}_1 \cdot \vec{r}_{12}) / |\vec{H}_1||\vec{r}_{12}|$$
$$\cos(\theta_2) = (\vec{H}_2 \cdot \vec{r}_{21}) / |\vec{H}_2||\vec{r}_{21}|$$
$$f(\theta) = \frac{1}{2}(\cos(\theta_1) + \cos(\theta_2))$$

wherein $\vec{r}_{12}$ is a vector between the two domain centers, $\theta_1$ and $\theta_2$ are angles between hydrophobic dipoles, $\vec{H}_1$ and $\vec{H}_2$, and the inter-domain distance vectors, respectively.

10. An article of manufacture for characterizing a multi-domain protein structure, comprising a tangible computer readable recordable storage medium containing one or more programs which when executed implement the steps of:
    for at least one domain, calculating a hydrophobic dipole, wherein calculating the hydrophobic dipole comprises referencing a structural feature of the at least one domain, and wherein calculating the hydrophobic dipole is carried out by a component executing on a hardware processor;
    calculating a score representing orientation of the hydrophobic dipole of the at least one domain relative to a hydrophobic dipole of one or more other domains of the multi-domain protein structure, wherein the score indicates an effect of one or more hydrophobic amino acid residues grouping near a region of domain contact, and wherein calculating the score is carried out by a component executing on a hardware processor;
    using the score to determine a bias in a domain hydrophobic dipole orientation within the multi-domain protein structure, and compare the score to a score of one or more native multi-domain protein structures to determine if the multi-domain protein structure resembles one or more native protein conformations, wherein determining a bias in a domain hydrophobic orientation comprises taking into account the calculated hydrophobic dipole of the at least one domain in the multi-domain protein structure, and wherein using the score to determine a bias in a domain hydrophobic dipole orientation within the multi-domain protein structure is carried out by a component executing on a hardware processor; and outputting the score representing orientation of the hydrophobic dipole of the at least one domain relative to a hydrophobic dipole of one or more other domains of the multi-domain protein structure to at least one of a user and a display.

11. The article of manufacture of claim 10, wherein the multi-domain protein structure comprises two domains.

12. The article of manufacture of claim 10, wherein the multi-domain protein structure comprises more than two domains.

13. The article of manufacture of claim 10, wherein the hydrophobic dipole comprises a first-order hydrophobic moment of the at least one domain.

14. The article of manufacture of claim 10, wherein the multi-domain protein structure comprises a single-chain multi-domain protein.

15. The article of manufacture of claim 10, wherein the multi-domain protein structure comprises an engineered protein structure.

16. The article of manufacture of claim 10, wherein an angle between the hydrophobic dipole and an inter-domain center-to-center distance vector common to the at least one domain and the one or more other domains is used to calculate the score.

17. The article of manufacture of claim 16, wherein the vector common to the at least one domain and the one or more other domains comprises an inter-domain distance vector.

18. The article of manufacture of claim 10, wherein calculating a score comprises calculating, for a two-domain protein, $f(\theta)$, wherein calculating $f(\theta)$ comprises calculating $$\cos(\theta_1) = (\vec{H}_1 \cdot \vec{r}_{12})/|\vec{H}_1||\vec{r}_{12}|$$
$$\cos(\theta_2) = (\vec{H}_2 \cdot \vec{r}_{21})/|\vec{H}_2||\vec{r}_{21}|$$
$$f(\theta) = \frac{1}{2}(\cos(\theta_1) + \cos(\theta_2))$$

wherein $\vec{r}_{12}$ is a vector between the two domain centers, $\theta_1$ and $\theta_2$ are angles between hydrophobic dipoles, $\vec{H}_1$ and $\vec{H}_2$ and the inter-domain distance vectors, respectively.

* * * * *